Figure 1:
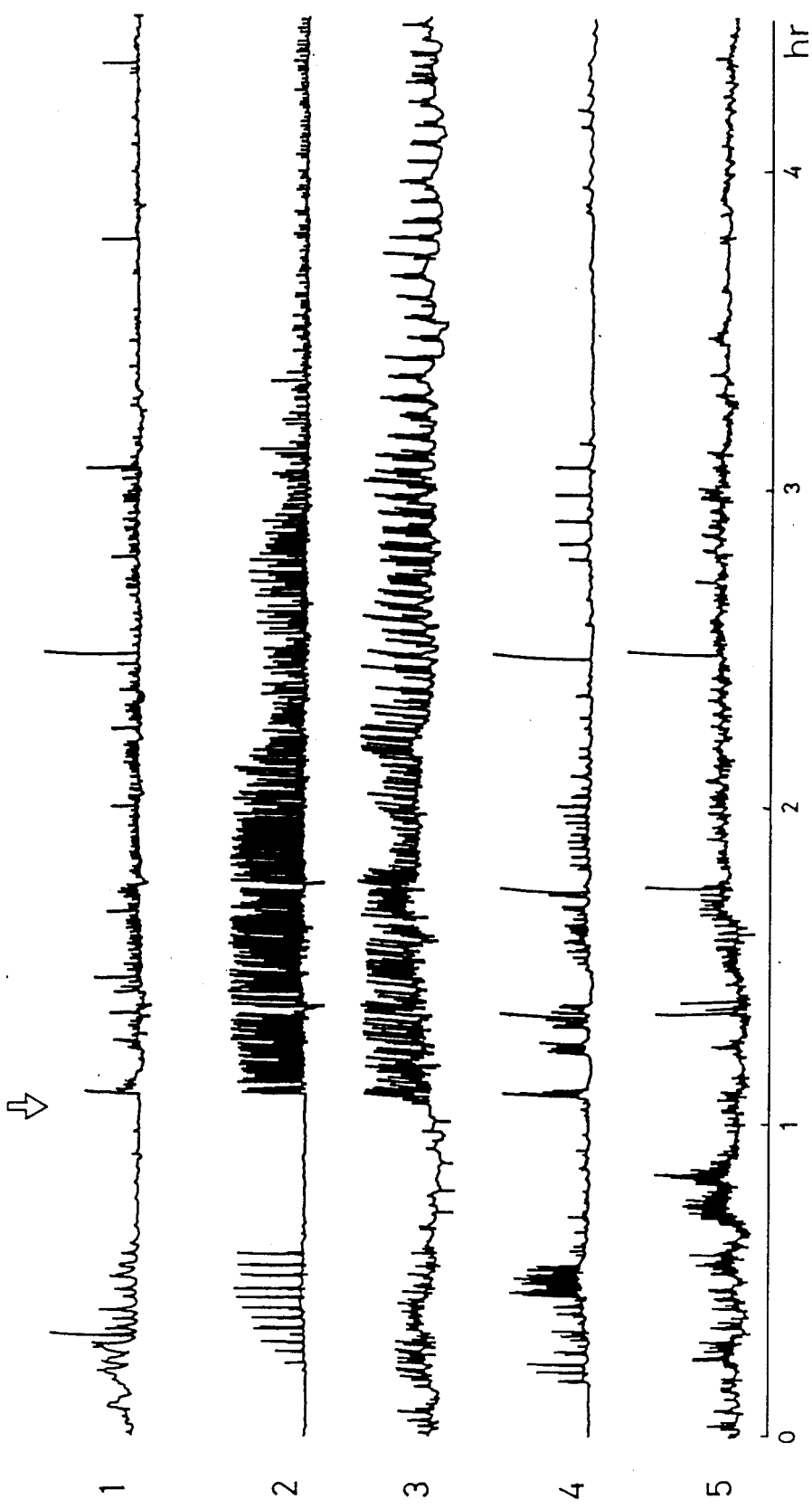

United States Patent [19]

Omura et al.

[11] Patent Number: 4,677,097
[45] Date of Patent: Jun. 30, 1987

[54] COMPOSITIONS FOR INDUCING CONTRACTILE MOTILITY OF THE GASTROINTESTINAL TRACT

[75] Inventors: Satoshi Omura, Setagaya; Zen Itoh, Maebashi, both of Japan

[73] Assignee: Kitasato Kenkyusho, Tokyo, Japan

[21] Appl. No.: 784,403

[22] Filed: Oct. 4, 1985

[30] Foreign Application Priority Data

Oct. 5, 1984 [JP] Japan ................... 59-209464

[51] Int. Cl.[4] ................ A61K 31/71; C07H 17/08
[52] U.S. Cl. ........................... 514/29; 536/7.2
[58] Field of Search ................... 514/29; 536/7.2

[56] References Cited

U.S. PATENT DOCUMENTS

| 3,674,773 | 7/1972 | Kurath | 536/7.2 |
| 3,681,323 | 8/1972 | Kurath et al. | 536/7.2 |
| 3,816,397 | 6/1974 | Tadanier et al. | 536/7.2 |
| 3,828,022 | 8/1974 | Tadanier et al. | 536/7.2 |
| 3,855,200 | 12/1974 | Krowicki et al. | 536/7.2 |
| 3,963,696 | 6/1976 | Martin et al. | 536/7.2 |
| 4,053,592 | 10/1977 | Smith et al. | 514/29 |
| 4,439,426 | 3/1984 | Toscano et al. | 514/29 |

*Primary Examiner*—Johnnie R. Brown
*Attorney, Agent, or Firm*—Wolder, Gross & Yavner

[57] ABSTRACT

A pharmaceutical composition for inducing contractile motility of the gastrointestinal tract in humans and animals, comprising as active ingredient 8,9-anhydroerythromycin 6,9-hemiketals, anhydroerythromycins, derivatives thereof and/or pharmaceutically acceptable salts thereof, in association with a pharmaceutically acceptable carrier or excipient. The active compounds may be produced by chemical modification of erythromycin and exhibit no or little antimicrobial activity. By administering the present composition to humans and animals, contractile motility of the gastrointestinal tract similar to the motility occurring naturally under normal conditions may be effectively induced.

6 Claims, 2 Drawing Figures

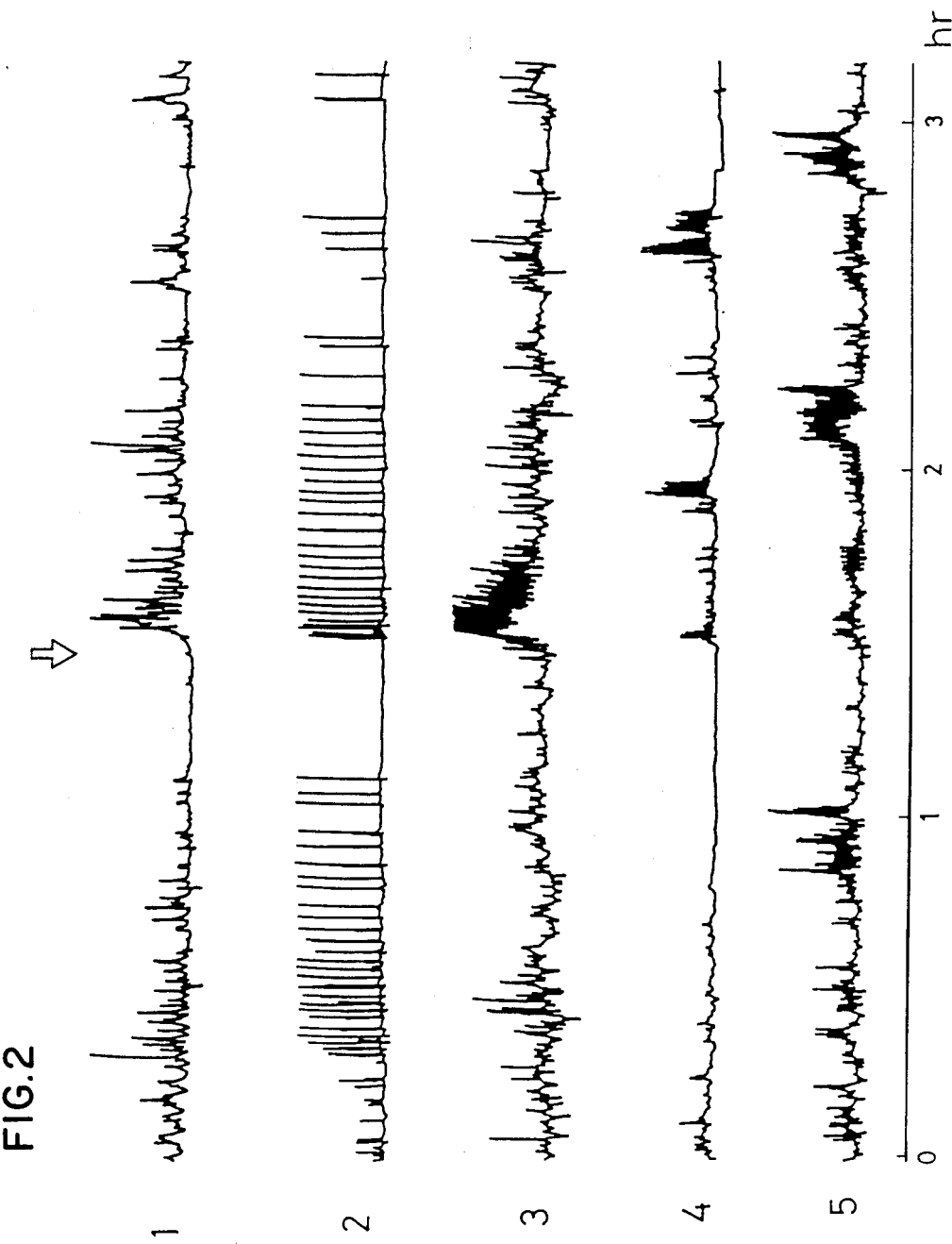

COMPOSITIONS FOR INDUCING CONTRACTILE MOTILITY OF THE GASTROINTESTINAL TRACT

FIELD OF THE INVENTION

The present invention relates to compositions for inducing contractile motility of the gastrointestinal tract of humans and animals.

BACKGROUND OF THE INVENTION

The gastrointestinal tract, which comprises the stomach, duodenum, small intestine etc., is very important for digesting foodstuffs fed through the oral cavity. The contractile motility of the gastrointestinal tract is indispensable for effective digestion of foodstuffs. In the case of healthy humans and animals, contractile motion is controlled by the autonomic nervous system as well as by gastrointestinal hormones and occurs with regularity not only in the digestive state, but also in the interdigestive state. In the latter state, the gastrointestinal tract is throughly cleaned before a subsequent meal as the contractile motility is transferred from the stomach to the small intestine through the duodenum.

The contractile motion of the gastrointestinal tract occuring naturally in the digestive state, i.e. immediately after a meal, shows continuous contraction waves, while the contractile motion occuring naturally in the interdigestive state shows intermittent waves with an interval of about 100 minutes. It is also known that a relationship exists between induction of contractile motion in the gastrointestinal tract and the concentration of the gastrointestinal hormone motilin in the blood. The concentration of this hormone in the blood decreases during feeding.

In the interdigestive state, contractile motion of the gastrointestinal tract correlates with a high concentration of motilin in the blood with reference to the reports by Zen Itoh, "Iden" (1979, Japanese version), Vol. 33, No. 12, pages 29–33; and Zen Itoh et al., Scand. J. Gastroent. (1976), 11, Suppl. 39. 93–110.

Agents for inducing contractile motility of the gastrointestinal tract are of interest for the treatment of humans suffering from poor function of the gastrointestinal tract, in order to improve the motility of the gastrointestinal tract and overall health.

It is known that motilin is capable of inducing motility of the gastrointestinal tract. J. C. Brown et al. extracted motilin from the duodenal mucosa of pig and reported that this substance is a peptide comprising 22 amino acids (J. C. Brown et al: Gastroent., 50, 333–339, 1966). The synthesis of motilin is also known (see, for example, B. Wunsch et al: Z. Naturforsch., 28C, 235–240, 1973). However, the supply of motilin extracted from natural souces and synthetic motilin is insufficient to satisfy practical needs.

One aspect of the present invention is based on the surprizing discovery that both erythromycin and 9-dihydroerythromycin and their pharmaceutically acceptable salts and derivatives are capable of inducing contractile motility of the gastrointestinal tract of humans and animals, and may be used to prepare pharmaceutical compositions for this purpose. However, erythromycin and 9-dihydroerythromycin are well-recognized antibiotics. From the point of view of maintaining the effectiveness of erythromycin and 9-dihydroerythromycin as antibiotics, it may not be desired to use these compounds for an alternative medical purpose.

Thus, another aspect of the present invention is based upon the further discovery that 8,9-anhydroerythromycin 6,9-hemiketals and anhydroerythromycins are also capable of inducing contractile motility of the gastrointestinal tract.

SUMMARY OF THE INVENTION

Thus this aspect of the present invention provides a pharmaceutical composition for inducing contractile motility of the gastrointestinal tract in humans or animals, which comprises as active ingredient at least one member selected from 8,9-anhydroerythromycin 6,9-hemiketals, anhydroerythromycins, derivatives thereof and pharmaceutically acceptable salts thereof, in association with a pharmaceutically acceptable carrier and/or excipient.

Suitable erythromycin derivatives for the preparation of a composition according to the present invention are thus, for example, the known compounds 8,9-anhydroerythromycin A 6,9-hemiketal, 8,9-anhydroerythromycin B 6,9-hemiketal, 8,9-anhydroerythromycin C 6,9-hemiketal, 8,9-anhydroerythromycin D 6,9-hemiketal and 8,9-anhydroerythromycin F 6,9-hemiketal (hereinafter referred to as type 1 compounds) and anhydroerythromycin A, anhydroerythromycin C and anhydroerythromycin F (hereinafter referred to as type 2 compounds).

As is well known, erythromycin is an antibiotic produced by various microorganisms of the genus Actinomycetes and exhibits high antimicrobial activity, in particular, against Gram-positive bacilli. Compounds of both type 1 and type 2 may be produced by chemical modification of erythromycins A, C and F. Compounds of type 2 are not obtainable from erythromycin B and D.

The known erythromycin derivatives which may be used to prepare compositions according to the present invention viz. anhydroerythromycin hemiketals and anhydroerythromycins have never been used in practice as antibiotics due to their poor antimicrobial activity (see, for example, Antibiotics Annual 1958-1959). Moreover, such erythromycin derivatives have, to our knowledge, never been used in practice for any other pharmacological purpose. It has now unexpectedly been found that these compounds are effective agents for inducing contractile motility of the gastrointestinal tract.

The compositions according to the present invention may be in any form conventionally used in the pharmaceutical art, for example, emulsions, hydrates, solutions, powders, granules, capsules or tablets.

Examples of pharmaceutically acceptable derivatives of erythromycin which may be used in the preparation of compositions according to the present invention include the ethylsuccinic acid esters, the ethylcarbonic acid esters, the glycopeptonates, the stearic acid esters, propionic acid esters, the lauric acid-propionic acid diesters, and the lactobionate.

Suitable additives which may be used are exemplified by various excipients, disintegrators, lubricants, binders, dispersants and plasticizers conventionally used in the pharmaceutical art.

Suitable excipients which may be used for the purpose of the present invention include, for example, lactose, glucose and sucrose. Suitable disintegrators include, for example, starch, sodium alginate, agar powders and calcium carboxymethylcellulose. Suitable lublicants are exemplified by magnesium stearate, talc and liquid paraffin. Suitable binders include, for example, simple syrup, gelatin solution, ethanol and polyvinyl alcohol. Suitable dispersants include, for example, methylcellulose, ethylcellulose and shellac and suitable plasticizers include, for example, glycerol and starch.

The composition of the present invention may be prepared by conventional pharmaceutical methods.

The administration of compositions of the present invention may be effected by conventional chemotherapeutic procedures, for example, parenterally (intravenously or subcutaneously), or orally. Preferred compositions may be in unit dosage form. Thus, it is possible to administer a composition of the present invention for example, by intravenous injection, at a daily dose of from about (on the basis of active ingredient) 0.001 mg/kg (for example 0.003 mg/kg) to about 10 mg/Kg (for example, 3 mg/kg). Usually, a daily dose of 5-10 fold amount may be used for oral administration on the basis of the dose for intravenous injection.

In a comparison of the gastrointestinal activities of type 1 compounds and type 2 compounds with the corresponding actvity of erythromycin in dogs, it has been found that it is usually possible to induce a contractile motion which is similar to the naturally occuring motion in the interdigestive state by intravenous injection of at a dose of, for example, 30–50 mcg/kg of erythyomycin, 3–5 mcg/kg of a type 1 Compound or 10–15 mcg/kg of a type 2 Compound.

However, the preferred dose may vary considerably depending upon the type of patient.

PREFERRED EMBODIMENTS

The following non-limiting Examples further inidicate the effectiveness of agents according to the present invention in inducing contractile motion of the gastrointestinal tract.

In these Examples, the contractile motion of the gastrointestinal tract was measured in the following manner with reference to a report by Zen Itoh ("Japanese Journal of Smooth Muscle Res., 1976, Vol. 13, No.1, pages 33–43 in Japanese version").

Systemic anesthesia and abdominal incision of a mongrel dog (adult; weight 10–15 kg) were effected to chronically implant force transducers on the serosal surface of the gastrointestinal tract from the stomach to the terminal ileum. Each force transducer was sutured on the serosa with sewing threads in a predetermined direction in order to measure the contraction of the corresponding circular muscle. A lead wire was brought out from each transducer and affixed to the skin at the back of the dog. It is, in general, possible to begin an experiment using a dog thus-treated on the 5th day after restoration of health and to use the dog over a period of about 6 months. Where a bending force is exerted as an implanted transducer, a contractile wave proportional to the bending force can be recorded on the graph paper of an oscillograph. In this manner, it is possible to study the characteristics and strength of any contractile motion.

The contraction wave may be recorded simply by connecting the lead wire of the transducer implanted in the conscious dog to a suitable polygraph. The contractile motions of the gastrointestinal tract may, in general, be classified into two types on the basis of their patterns observed in the digestive state and the interdigestive state. The experiments of the Examples were effected in the interdigestive state after termination of contractile motion in the stomach.

Before each experiment, silastic tubing was chronically implanted into the superior vena cava through the external jugular vein. Through this tubing a sample of the erythromycin derivative under investigation was injected slowly over a period of about 10 seconds. The erythromycin derivative was dissolved in physiological saline to give a sample volume of 10 ml.

EXAMPLE 1

1.0 mg/kg of 8,9-anhydroerythromycin A 6,9-hemiketal was administered by intravenous injection to a dog prepared as described above. FIG. 1 shows the contractile motions observed in the gastric body (1), gastric antrum (2), duodenum (3), upper jejunum (4) and lower jejunum (5). The arrow indicates the time of the injection.

Immediately following administration of 8,9-anhydroerythromycin A 6,9-hemiketal, very strong contractions were induced in the various portions of the gastrointestinal tract under study. The contractions gradually subsided. The resultant contractile force was similar to the strongest contractile force observed in the gastrointestinal tract of dog under normal conditions.

EXAMPLE 2

A similar experiment to that described in Example 1 was carried out using anhydroerythromycin A. The results obtained when anhydroerythromycin A was administered by intravenous injection at 1.0 mg/kg are shown in FIG. 2, from which it can bet seen that the resultant contractile force was somewhat weaker than the contractile force obtained in Example 1. In this figure, numerals 1, 2, 3, 4 and 5 respectively indicate the gastric body, gastric antrum, duodenum, upper jejunum and lower jejunum as FIG. 1, and the arrow indicates the time of the intravenous injection.

As is apparent from FIGS. 1 and 2, strong continuous contractile motions are induced in various portions of the gastrointestinal tract of a dog immediately after intravenous injection of 8,9-anhydroerythromycin 6,9-hemiketal or anhydroerythromycin A at a dose of 1.0 mg/kg. The patterns shown in FIGS. 1 and 2 are similar to the naturally occuring patterns in the gastrointestinal tract of humans and animals in the digestive state. It has also been found that intermittent contractile motions which are very similar to the naturally occuring patterns observed in the gastrointestinal tract of humans and animals under normal conditions may be induced by administering a smaller amount of 8,9-anhydroerythromycin 6,9-hemiketal or anhydroerythromycin.

We claim:

1. A method for inducing contractile motility of the gastrointestinal tract of an animal subject which comprises administering an effective amount of an active ingredient selected from the group consisting of 8,9-anhydroerythromycin A 6,9 hemiketal; 8,9 anhydroerythromycin B 6,9-hemiketal; 8,9-anhydroerythromicin C, 6,9-hemiketal; 8,9-anhydroerythromycin D, 6,9-hemiketal; 8,9-anhydroerythromycin F 6,9-hemiketal; anhydroerythromycin A, anhydroerythromycin C, anhydroerythromycin F; erythromycin derivatives thereof and pharmaceutically acceptable salts thereof; such active ingredient being admixed with a pharmaceutically acceptable carrier or excipient.

2. The method of claim 1 wherein said active ingredient is administered by intravenous injection at a daily dosage of from about 0.001 mg/kg to about 10 mg/kg of body weight based on active ingredient.

3. The method of claim 1 wherein one composition is administered orally at a daily dosage of 5 to 10 times the range to 0.001 to 10 mg/kg of body weight.

4. The method of claim 1 wherein the derivative employed is an erythromycin derivative selected from the group consisting of ethylsuccinic acid esters, ethylcarbonic acid esters, glycopeptonates, stearic acid esters, propionic acid esters, lauric acid-propionic acid diesters and lactobionate.

5. The method of claim 1 wherein the composition is administered in a form selected from the group consisting of emulsion, hydrate, solution, powder, granules, capsules and tablets.

6. The method of claim 2 wherein said active ingredient is administered by intravenous injection at a dose of 1.0 mg/kg.

* * * * *